United States Patent [19]
Dachman

[11] Patent Number: 4,981,142
[45] Date of Patent: Jan. 1, 1991

[54] COMPRESSION DEVICE

[76] Inventor: Abraham H. Dachman, 717 Sonato Way, Silver Spring, Md. 20901

[21] Appl. No.: 214,026

[22] Filed: Jun. 24, 1988

[51] Int. Cl.⁵ .............................................. A61B 10/00
[52] U.S. Cl. .................................. 128/749; 128/897; 604/116; 376/204
[58] Field of Search .......................... 248/231, DIG. 6; 378/37, 204, 208; 604/116, 117; 128/303 R, 630, 644, 662.05, 749, 751, 754, 763, 750, 898, 897

[56] References Cited

U.S. PATENT DOCUMENTS

| | | | |
|---|---|---|---|
| 1,484,001 | 2/1924 | Ainsworth | 248/DIG. 6 |
| 2,703,359 | 3/1955 | Miller | 248/231 |
| 3,241,800 | 3/1966 | Richter, III | 248/231 |
| 4,347,850 | 9/1982 | Kelly-Fry et al. | 128/915 |
| 4,798,212 | 1/1989 | Arana | 128/749 |

Primary Examiner—Max Hindenburg
Assistant Examiner—Randy Shay

[57] ABSTRACT

The present invention relates to the construction and use of a device to compress biological parts (such as the abdomen), during the performance of interventional procedures (such as percutaneous biopsy), guided by cross sectional imaging procedures (such as computed tomography). The device is composed of a compressive surface with a hole. The compressive surface is constructed as part of a downward protruding member and lateral flanges or a rim, which can be attached, for example, to an abdomen, by means of a strap mechanism. An optional back plate can be used, such that a strap mechanism compresses the body part between the back plate and compression plate, or the compression plate alone can be place. The device can remain in place during cross sectional imaging, provided effective compression of the animal or human body part, yet access for percutaneous intervention is maintained by means of the hole in the compression surface.

10 Claims, 2 Drawing Sheets

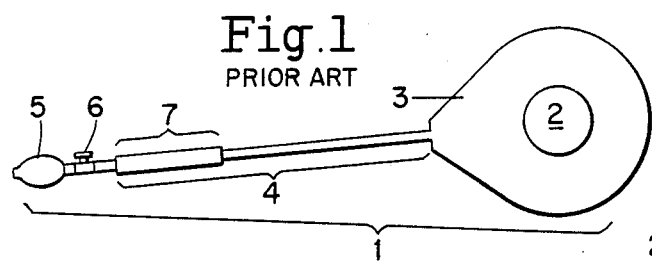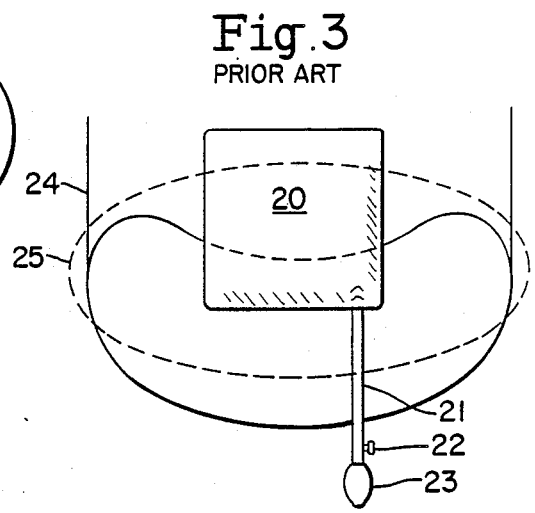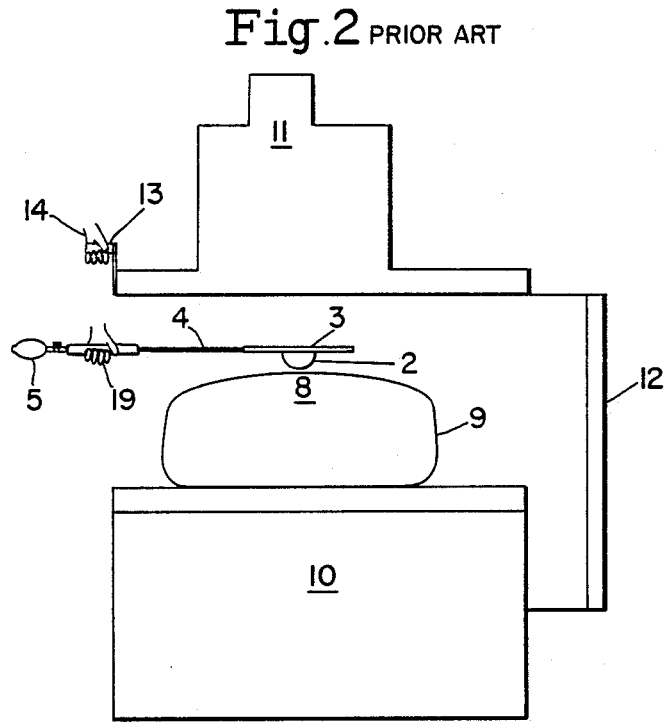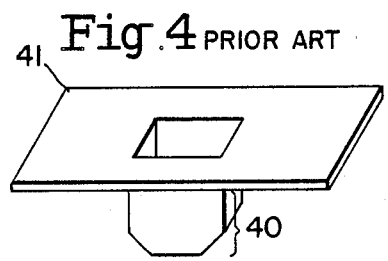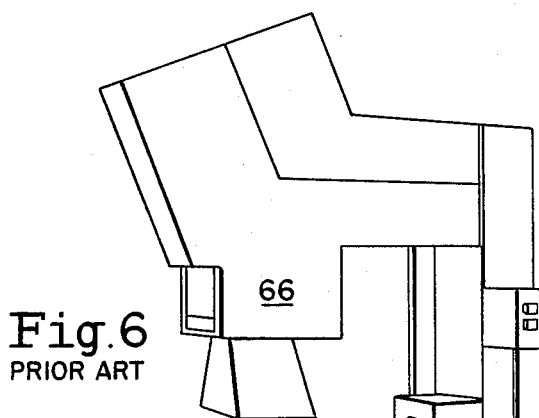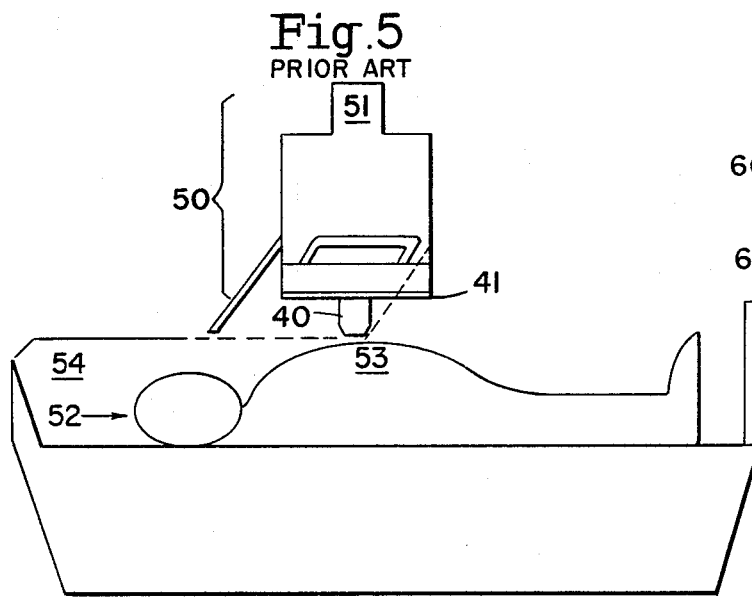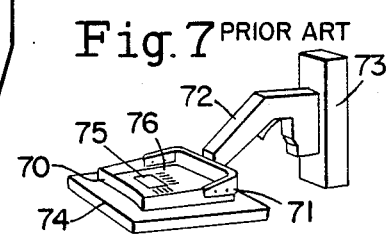

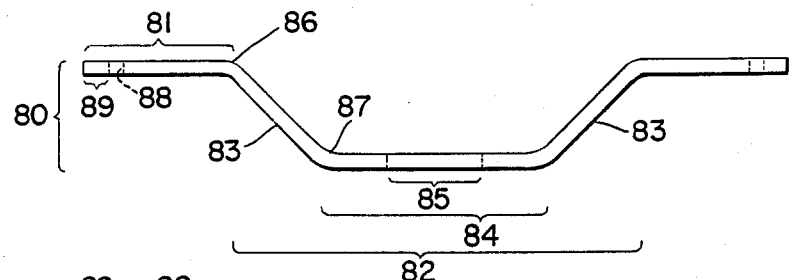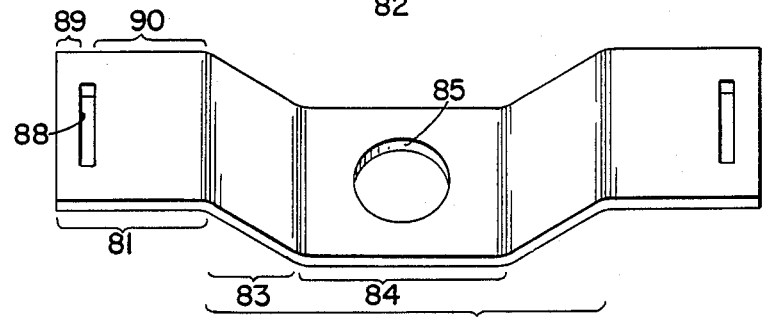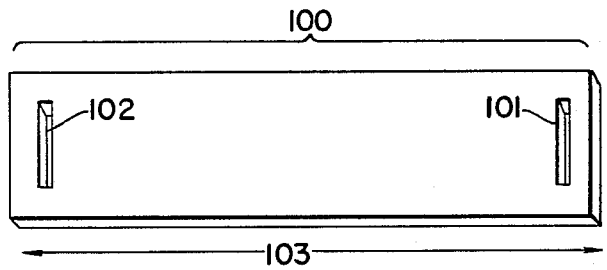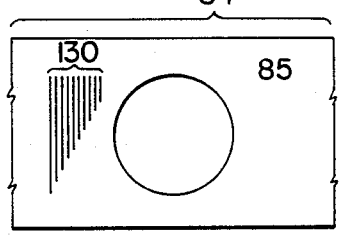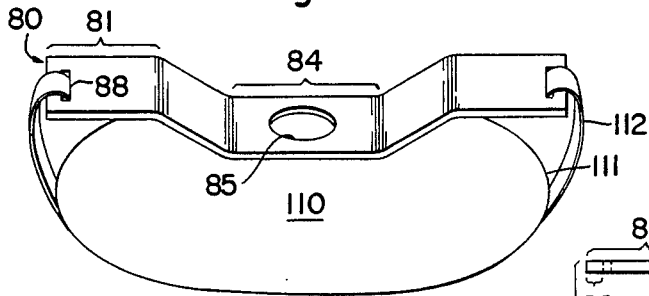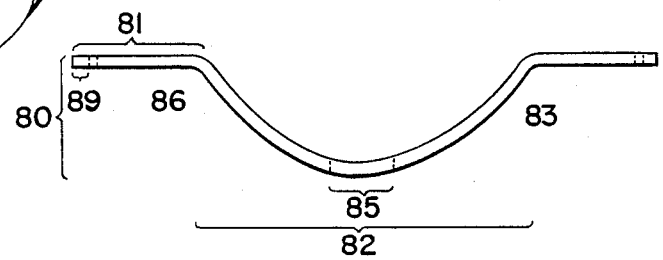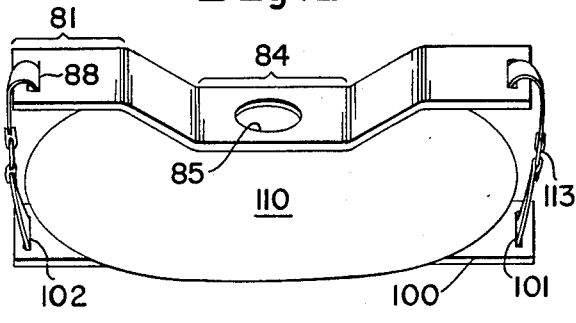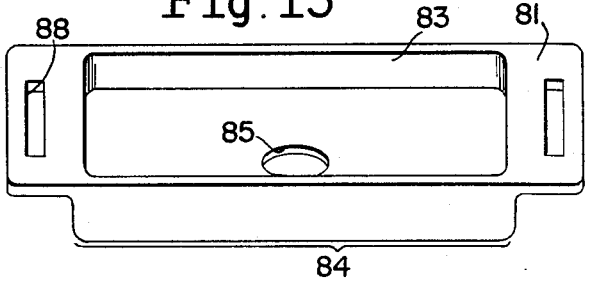

COMPRESSION DEVICE

BACKGROUND OF THE INVENTION

I. Field of the Invention

The invention relates generally to a device designed for human or animal use in biological imaging procedures such as: computed tomography, sonography, and magnetic resonance imaging. The invention also relates to the use of such a device.

II. Prior Art

A. Compression Devices

Compression devices are devices which compress parts of the body for diagnostic purposes as will be subsequently described herein. Such compression devices are available for use, for example, in fluoroscopic procedures (real time visualization of body parts by use of x-rays) and in mammography (breast x-rays). Compression devices may be either balloon type or rigid type, and may be used by hand or by remote control.

With reference to FIGS. 1 and 2, an example of the most commonly used compression device, termed a "paddle", will be described. It is of the balloon type and is used by hand during the performance of fluoroscopic procedures such as an upper gastrointestinal series or barium enema. As shown in FIG. 1, the paddle (1) consists of a rubber balloon or bladder (2) which is attached to a rigid backing (3). The balloon is connected via rubber tubing encased in a long rod (4) to a an inflation bulb (5). The air flow is controlled by a valve (6). If the valve is closed, squeezing the inflation bulb repeatedly, will insufflate the rubber balloon with room air such that it forms a hemispherical shape. The device is held at the handle grip (7), with the rubber bladder facing downward, allowing the user to position the rubber bladder, for example, on a patients abdomen (8) within the x-ray beam, under fluoroscopic guidance. The length of the rod permits the user to keep his hand at a distance, outside the x-ray beam. FIG. 2 is a head on view of a patient (9), lying flat on an x-ray table (10). The tower (11), contains the parts which produce the x-rays. The tower can be moved up and down on an armature (12), by holding the handle (13) and moving it in the desired direciton. Compression of the abdomen is achieved in one of two ways. In one method the user's hand (19) exerts a downward force on the compression device's handle grip (7). This manual downward force compresses the patient's abdomen (8) between the balloon and the table. Alternately, compression is achieved by first positioning the balloon over the desired patient part with one hand (19). Then with the user's other hand (14), moving the tower downward, such that the weight of the tower plus the downward force applied to the tower's handle, exert a downward force on the back of the paddle's rigid backing (3), thus compressing the patient's abdomen between the table and the balloon.

Another balloon type of compression device is the "compression bladder." With reference to FIG. 3 the usage of a compression bladder will be described. The compression bladder consists of a circular or rectangular rubber balloon (20) with a segment of tubing (21). A valve (22) is attached to the tubing, to which an inflation bulb (23) is attached. The bladder is positioned in the desired location on the patient's body (24) shown in cross section. It is then secured in place by a compression band (25) which is tied around the patients body and secured, for example, by velcro. Compression is then achieved by insufflating the rubber bladder with room air by repeatedly squeezing the inflation bulb. The inflated bladder compresses the body since it is fixed in place by the band. This is often used to provide pinpoint pressure, for example, during kidney x-rays (excretory urography) for compressing the ureters.

A rigid compression device is generally known as a compression cone. With reference to FIGS. 4 and 5 a compression cone will be described. The compression cone is designed to be attached to an x-ray machine (50), but not directly to a patient. It can be used as a hand-assisted device attached to an x-ray tower (51), or as a remote controlled compression device. It consists of a cone or rectangular shaped elevated portion (40), which lacks a hole, attached to a base plate (41). The base plate attaches to the tower (51) of the x-ray machine. Compression is applied by positioning the patient (52) such that the desired body part (53) is directly under the cone, and moving the tower downward to squeeze the body between the table top (54) and the tower (51). Alternately, not shown in these figures, the cone is attached to a separate mechanized arm which can be positioned by remote control and also moved up and down by remote control to effect variable compression. The use of remote control allows the radiologist to perform the procedure without exposing himself to scatter radiation in the examining room.

There are also flat, rigid compression devices, devised specifically for compression of the breast during mammography. The purpose of compression of the breast in mammography includes: separating structure within the breast, reducing the distance between the x-ray film and the breast, and reducing overall thickness of the breast to get a better quality picture with less radiation. With reference to FIG. 6 a flat mammography compression device will be described. This device is composed of a generally flat, rectangular plate (60) attached to a frame (61). The frame in turn, is attached to an arm (62), connecting the device to part of the tower (63). Some models allow for angulation of the compression plate as well (not shown in this figure). Compression the breast against a platform (65) is achieved by manually adjusting the arms and sliding the flat plate downward, and locking the adjustment lever. The flat shape of the plate is desirable for compressing a small, soft structure, such as the breast. It would be undesirable for compressing an abdomen. Some similar devices are not attached to the mammography unit, but are mounted to it by suction cups, or tied to the platform with a strap. After the device is positioned, x-rays are produced from the x-ray tube within the housing (66), producing an exposure of the cassette place within the platform (65).

B. Mammography Compression Biopsy Guides

A biopsy is a procedure whereby a sample of biologic tissue is obtained, usually by placement of a needle designed to trap tissue, or by attaching a syringe to the needle and suctioning. Needles are commonly placed in breast tissue, either for biopsy, or to remain in the breast and serve as a guide to surgery.

The only device which both compresses tissue and serves as a portal for a biopsy, is a mammography localization device for biopsy. With reference to FIG. 7 an example of a mammography localization device for biopsy will be described. In this example, this device is identical in shape and in attachment to the mammography machine as shown in FIG. 6. FIG. 7 also shows the compression plate (70), frame (71), arm (72), part of the tower (73) and the platform (74). The critical difference in FIG. 7 is a rectangular cut-out which serves as the biopsy portal (75). At the edges of the portal, there are lines (76) etched into the device, which are radiopaque (can show up on x-ray film). These lines serve as a graph to guide placement of the needle. One row serves as an "x-coordinate" and the other row as a "y-coordinate" in localizing the mass on the developed x-ray film. The radiologist then enters the room, and uses these lines on the device as an optical guide to select the site on the patient's skin most likely to be directly overlying the breast mass.

With respect to mammography biopsy localizers, there are other designs, which may form a radiopaque grid over the biopsy portal. Some devices may not attach to the mammography machine tower, but rather to the platform by use of suction cups on a series of supporting arms. Some devices are placed over the breast, and tied around the platform to secure them.

C. Imaging Biopsy Guides

Cross sectional imaging procedures are methods that visualize a "slice" of internal anatomy. An example of an imaging procedure is computed tomography (CT). CT is a method whereby x-rays and computers are combined to produce a picture of a "slice" of a body. Percutaneous (through the skin) procedures are interventional procedures whereby a needle, catheter or similar appliance ia placed internally via a skin puncture, usually under radiologic guidance. Radiologic guidance may include, for example, fluoroscopy, or cross sectional imaging procedures, such as CT, ultrasound, and magnetic resonance imaging (MRI). For example, the placement of a needle, for the biopsy of an internal body part often requires CT guidance to place the needle tip in the desired internal location. CT and ultrasound are commonly used to guide placement needles for biopsies or similar procedures. Using the example of a CT guided biopsy, the method is as follows. A CT scan is first performed to localize a mass. Each CT "slice" is labelled by the position of the table or patient with respect to the gantry (x-ray portal). The slice showing the mass is selected and used to chose an anatomic approach for needle placement. With the x-ray off, the radiologist enters the room and using standard sterile technique, places the needle through the skin overlying the mass. The CT slice is repeated to prove that the needle has in fact been successfully placed within the mass.

Difficulty in needle placement may arise due to a variety of reasons. Firstly, it may be desirable to avoid some structures in the ideal needle path, forcing use of a less desirable path. Secondly, a desirable needle path may not be usable due to a surgical appliance or skin lesion overlying the lesion. Thirdly, a long needle path may make accurate placement with a minimum number of tries, difficult. This is because of the geometry of the patient; if there is a longer distance from the skin to the mass, a minor "off-course" angulation at the skin insertion site is amplified at the needle tip. Thus a small mass may require a number of needle passes until it is punctured placed. This problem is accentuated when performing percutaneous procedures on obese individuals.

A number of devices have been devised to assist in accurate imaging or CT guided needle placement. For example, a grid that shows up on CT images may be placed over the patient's skin to assist in locating the skin directly overlying a lesion. Another example is a stabilization device for intracranial CT guided biopsy (published in RADIOLOGY 144:183–184,1982). This device stabilizes the head within a ring-frame, with an adjustable needle guide along the upper circumference of the frame. Another example is the use of injected carbon dioxide (relatively harmless in the abdominal cavity), to move internal structures blocking the most desirable needle path, out of the way (published in RADIOLOGY 161:829–830,1986).

None of the existing devices used in cross sectional imaging percutaneous procedures, allow the operator to move internal structures out of the way by using compression. None of the existing compression devices are designed for use in cross-sectional imaging procedures. Only the mammography biopsy localization device combines compression with a biopsy portal. Unlike this invention, the mammography biopsy guide is not designed for use in cross sectional imaging, it is not shaped to provide compression to deep structures, and does not attach independently to the patient's body. For example, since the mammography biopsy guide is flat, it will not provide adequate compression for a patients abdomen.

SUMMARY OF THE PRESENT INVENTION

The use of the present invention improves the diagnostic capacity of cross sectional imaging by allowing compression, and permits imaging-guided percutaneous procedures while the compression remains in place. Compression in cross sectional imaging can decrease the distance between the skin and the target, allowing more accurate needle placement with fewer tries. This is highly desirable, for example, in obese patients. Compression of the abdomen, for example, might allow an anterior (ventral) approach for some retroperitoneal (near the back) lesions, that would otherwise be hard to needle from a posterior approach without inadvertently puncturing kidney or aorta.

Similar advantages would apply, for example, in all percutaneous procedures, such as biopsy, percutaneous drainage procedure, or injection of chemicals for therapy (such as celiac plexus nerve block, which is injection of a chemical in a cluster of internal nerves in the upper abdomen to relieve intractable pain). Likewise, these advantages of compression would be useful in imaging procedures other than CT, such as ultrasound, magnetic resonance imaging (MRI), etc.

The object of the invention is to enable compression of a specific part of an animal or human body (for example, the abdomen), during cross sectional imaging, yet maintain access directly over the compressive surface of the device for percutaneous intervention (for example, needle or catheter placement) using imaging guidance.

The use of the invention ("device") will be discussed in terms of application with computed tomography (CT), with the understanding that other imaging modalities such as ultrasound, magnetic resonance imaging, positron emission (PET) scanning etc., are within the invention and have identical applications.

In carrying out the above object, the following criteria must be satisfied: (A) The device should be easily applied, positioned, adjusted yet remain in place during scanning. (B) The device should not significantly interfere with image quality during scanning. (C) The device should provide effective and variable compression to the human or animal body. (D) The device should permit access to a sufficient area of skin to permit cleaning of the skin and access for percutaneous needle puncture, without requiring removal or adjustment. (E) The device should significantly decrease the distance between the lesion to be targeted and the skin. Criteria A–E, should be accomplished with compromising access to the patient's skin (i.e. the device can not be excessively deep or have a geometry that might prevent easy access to the patients skin at the needle insertion site).

The device should be constructed of a material that will not cause artifacts when used. Artifacts are undesirable signals that interfere with true anatomic image production. This means, for example, that when used in CT, the device should not be of a radiographically dense metal, but may be constructed of plastic, plexiglass, acrylic, ceramic, wood, relatively radiolucent metals, and other relatively radiolucent material. Likewise, when used in magnetic resonance imaging (MRI), it will be made of a material that does not cause artifacts in MRI.

BRIEF DESCRIPTION OF THE DRAWINGS

FIG. 1: Compression paddle

FIG. 2: Compression paddle in use viewed from the patient's feet.

FIG. 3: Perspective view of a compression bladder, with a patients abdomen shown in cross section.

FIG. 4: Rigid compression cone, side view with cone facing downward

FIG. 5: Rigid compression cone in use, side view of x-ray machine

FIG. 6: Mammography machine with compression device attached

FIG. 7: Perspective view of a mammography compression biopsy localizer

FIG. 8: Side view of invention compression plate

FIG. 9: Top perspective view of invention compression plate

FIG. 10: Top perspective view of optional back piece for the invention.

FIG. 11: Perspective cross section of a patient with the invention compression device in place.

FIG. 12: Perspective cross section of a patient with the invention compression device and the optional back piece in place.

FIG. 13: Close-up top view of central part of compression surface with etched radiopaque guide lines.

FIG. 14: Side view of compression plate with the downward protruding member having a rounded shape.

FIG. 15: Top perspective view of invention compression plate having one wall.

DETAILED DESCRIPTION OF THE PREFERRED EMBODIMENT

The device consists of a compression plate and an optional back piece. With respect to FIGS. 8 (a side view) and 9 (a top view) the compression plate will be described. The compression plate (80) consists of a single piece. The lateral flat part, on either side are the flanges (81). The central part is the downward protruding member (82) (the "nose"), having sidewalls (83) and a compression surface (84). The compression surface (84) contains a central hole (85). The junction (86) of the flange and the sloped part (i.e. the sidewalls) (83), can be rounded or sharply cornered. The junction (87) of the sloped sidewall and the central part is preferably rounded to avoid irritating the skin. Each flange (81) has a slot (88) at its outer end. The slot thus divides the flange into a small outer lip (89), and a longer major segment (90).

With reference to FIG. 10 an optional back piece of the invention will now be described. This is a flat rectangular plate (100), made of a material having the same criteria as the material of the compression plate. Rectangular slots (101,102) are cut out or otherwise provided on either side. The slots on the back piece are preferably of the same dimension as the slots on the compression plate. The length (103) of the back piece should preferably be the same as the compression plate.

The use of the device includes the addition of a strap-like material, or any other means that will secure the compression plate as pointed out herein, and is demonstrated in FIG. 11 without use of the back piece, and in FIG. 12 with use of the optional back piece. FIG. 11 is a cross section of a patient's abdomen (110) viewed from the patient's feet. The compression plate (80) is in place, showing the compression surface (84) compressing the patient's abdomen (110). The flanges (81) extend laterally in a horizontal fashion beyond or near the patient's flank (111). A gradable degree of compression is achieved, for example, in one of several ways: by an adjustable length strap (112) of material (such as cloth, VELCRO, leather, canvas or nylon) placed around the patient (110) and attached to slots (88) as shown in FIG. 11. The strap may be self adhering (VELCRO), or be sewn to one end and tied to the other (for example, by a non-metallic snap, clip or buckle). Alternately, compression is achieved by a strap sewn to one end and threaded through a double slit assembly on the other end which is self sealing and not requiring a buckle or clip, or by attachment to the optional back piece and adjusting the length of the strap mechanism to achieve the desired degree of compression (FIG. 12).

The compression plate may be made from a choice of materials which are standard for radiologic devices. These materials and methods of production are widely used to produce compression devices and patient restraints. They include plastics, polymers, polycarbonate, acrylics, wood, and any other materials which are non-radiopaque or minimally radiopaque. They are of such form and thickness to withstand the stress, pressure and forces applied to the device.

Although shown as a single piece, the device could be a plurality of integrally and rigidly bonded pieces. Rather than two extending flanges, the device could consist of a plate with a hole in it having walls. The flange, (81) of FIG. 8, could extend all the way around, to form a rim around the downward member (82). Although the sidewalls (83) are shown as sloped they may be perpendicular or any other shape which will provide the inventive compression. The downward protruding member (82), could have four walls, or could form a cone, or could otherwise be an enclosed surface extending downward from the rim. The compression surface (84), although shown as flat could be curved to provide effective compression (for example rounded or spoon shaped).

FIG. 14 is a representation, for illustrative purposes, of the case where the downward protruding member forms a rounded shape. All reference numbers in FIG. 14 are analogous to those previously described.

FIG. 15 is a representation of the case where the downward protruding member has one wall. All reference numbers in FIG. 15 are analogous to those previously described.

The device may be modified to include radiopaque markers to help guide positioning (see FIG. 13). FIG. 13 is an enlarged top view of the compressive surface

(84) and its central hole (85), showing optional radiopaque markers (130). The markers are made by etched grooves in the plastic coated with a lead based paint. The concept and method of making such markers are known in the production of radiologic devices. The concept of alternating the length of linear markers on CT is also not new.

The materials for strapping the device in place are standard. The strap mechanism should be adjustable to provide variable compression and removal. The strap recommended is a 2 inch wide canvas or coarse weave nylon strap. It is sewn onto one wing of the compression plate. After positioning the device, the strap is inserted in the double slit of the opposite wing. The double slit construction, with angulation of the outer slit is designed to keep the strap fixed in place. Alternately, a clip or buckle may fix the strap in place. These clips and buckles are made of a plastic and are standard (as used in baby restraints, high chairs etc.). When used with the optional back piece, both straps on either end of the compression device, extending to the respective end of the back piece, should be adjustable, and at least one of the two straps should be removable or have a buckle or similar mechamism. Alternately, a VELCRO-type strap may be used with the hook and loop combined (as made by AllMed, Inc., Dedham, Mass. and termed "Alistrap").

EXAMPLE

An example of the present invention will now be described: The compression plate (80) is constructed of a single piece of polycarbonate of ¼ inch thickness, molded to form the shape shown in FIGS. 8 and 9 with the following dimensions:

| | |
|---|---|
| compression plate (80) | length = 17 inches, width = 5 inches. |
| flange (81) | length = 5.5 inches |
| lip (89) | length = .5 inch |
| major segment (90) | length = 4.75 inches |
| slot (88) | 2 inches long, width = .75 inch. |
| junctions (86,87) | 50 degrees with a curve of 1 inch radius. |
| sloping walls (83) | length 2.5 inch. |
| The right triangular shape thus formed by the sloping wall (83) as the hypotenuse, and a perpendicular dropped from junction (86), would form a base 1.5 inches long. | |
| compression surface (84) | length = 4 inches |
| hole (85) | centrally place in compression surface, radius = 1 inch. |

In this example the recommended size of the hole is two inches in diameter to allow this area of the patient's skin to be swabbed with a bacteriostatic solution as is routine in needle punctures.

The recommended procedure for use of the device is as follows. The device is placed over the area of interest and the patient is scanned. It may be repositioned if necessary, or positioned on the basis of a "scout" image which is compared with a prior CT scan for external landmarks. The device position is marked on the skin in ink. The device is removed, the skin prepared and draped. A hole is made in the drape to conform to the hole in the compression surface (84). The plate is again fixed in place. If the sterilized skin is contaminated, it may be re-swabbed with the plate in place. A second drape is placed over the compression plate. The patient is scanned, and the needle is placed the usual fashion. The radiopaque markers may be used to guide positioning of the needle.

I claim:

1. A biopsy compression device comprising:
   a compression surface having a hole for receiving a biopsy device therethrough;
   a wall or walls extending at an angle from said compression surface, the wall or walls being connected to the compression surface at a first end of the wall or walls;
   two flanges or a rim extending from the end of the wall or walls opposite to the first end;
   a connection means located on each of the two flanges, or at diametrically opposed ends of the rim;
   fastening means for extending completely around a portion of a human body connected to each of said connection means, such that the fastening means can be loosened or tightened.

2. The device of claim 1, wherein:
   the connection means are slots, the wall or walls are two walls, the two flanges or rims are two flanges connected to and extending away from each of the two walls, with the two walls being sloped at an angle with respect to both the compression surface and the flanges.

3. The device of claim 1 or claim 2 wherein the hole in the compression surface is at least large enough for needle placement and wherein the point at which the compression surface and wall or walls meet is smooth and without any sharp corners and has only smooth curves.

4. The device of claim 1 wherein:
   the compression surface and wall or walls define a downward protruding member which is curved to form a rounded compression surface capable of producing significant compression when applied to a biological part of an animal or human, such as the abdomen.

5. The device of claim 4 wherein:
   the biological part is the abdomen and the device is structured and shaped so as to provide compression to said abdomen.

6. The device of claim 1 or claim 2 wherein:
   the device is structured and shaped so as to provide compression to said abdomen and the device is of a material which will allow production of a CT image or MRI image of diagnostic quality.

7. The device of claim 1 wherein:
   said two flanges or rim extend for a sufficient length to attach a fastening strap mechanism or belt mechanism.

8. The device of claim 1 further comprising:
   a curved or straight piece for placement on a human back which is indirectly fastened to the two flanges or rim via said fastening means to provide a compression force on the two flanges or rim.

9. A method of using the device of claim 1, wherein:
   the device of claim 1 is used to apply compression to a biological part of an animal or human, by tightening said fastening means.

10. The method of claim 9 wherein:
    the biological part is the abdomen.

* * * * *